March 23, 1948. F. D. WILLIAMS Plant Pat. 795
PEACH TREE
Filed March 23, 1946
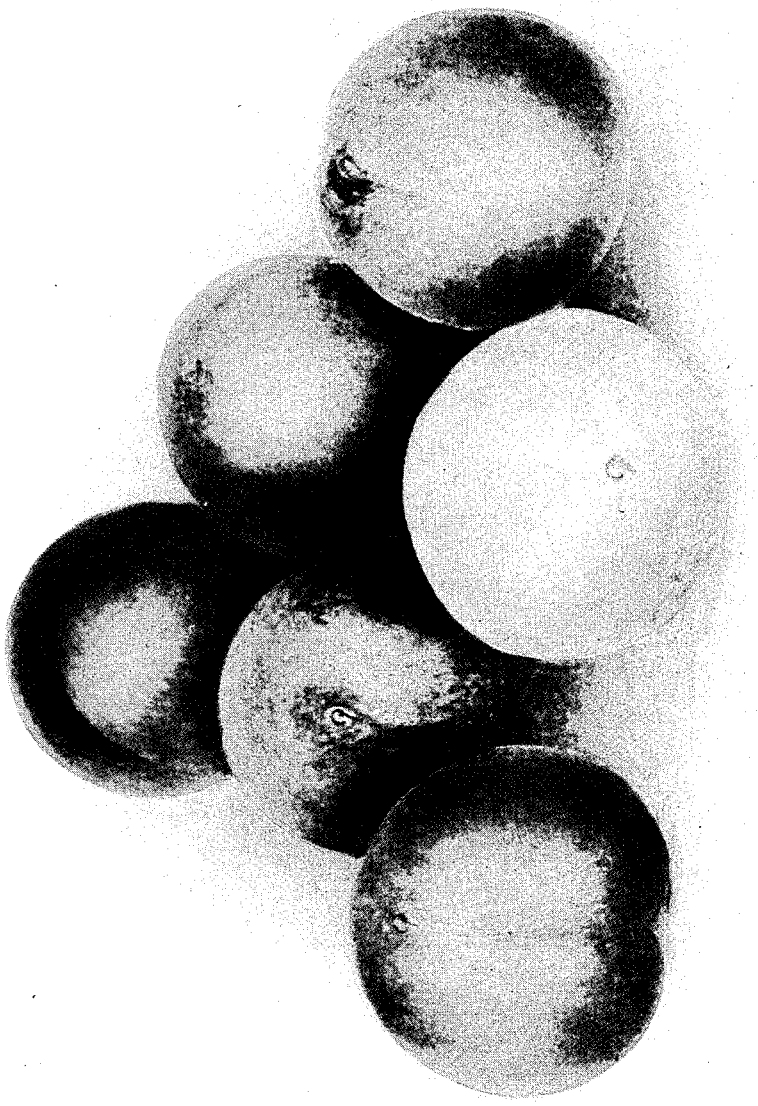
WITNESS
Addison E. Avery
INVENTOR
F. D. Williams
Webster & Webster
ATTYS.

Patented Mar. 23, 1948

Plant Pat. 795

UNITED STATES PATENT OFFICE

795

PEACH TREE

Fred D. Williams, Porterville, Calif.

Application March 23, 1946, Serial No. 656,593

1 Claim. (Cl. 47—62)

This discovery relates in general to a new and distinct variety of peach tree, and in particularity to a peach tree having freestone fruit of which the novel characteristics can best be understood by comparison with the Elberta, or the Fay Elberta, varieties of peach.

The present discovery is a peach tree which bears freestone fruit having the favorable characteristics of the Elberta and Fay Elberta varieties, but in addition is distinguishable by the higher coloring of the skin of the fruit, and the almost total lack of fuzz thereon. The color is predominantly deep reddish, and which coloring tends to be slightly mottled.

While beneficially distinguished from the Elberta and Fay Elberta varieties by such higher coloring of the fruit, and almost total lack of fuzz thereon, this new variety equals the others in ability to bear, tree vigor, size of crop, freedom from disease, and keeping quality of the fruit; and the fruit retains the rich acceptable flavor that has made the Elberta and Fay Elberta varieties popular in the trade.

Another distinguishing characteristic of the fruit of this new variety is that the astringent and somewhat bitter taste that is found near the pit in the flesh of the Elberta, and to a lesser extent in the Fay Elberta, is lacking.

A further distinction between the fruit of the present variety, as compared to the Elberta, is that the fruit remains very firm even when ripened to the extent which imparts the high coloring thereto. This is in contrast to the Elberta, which starts to soften before much coloring appears on the skin.

The present variety was discovered by me in my orchard at Poplar, Tulare County, California, as a bud sport on a Fay Elberta peach tree. Since the date of such discovery the new variety has been successfully asexually reproduced. The trees of the new variety, as so asexually reproduced, have come into bearing, and it is found that the fruit thereof maintains, in full, the novel and advantageous characteristics of the fruit of the original tree.

The figure is a photographic reproduction, in full coloring, of a group of the fruit of the herein claimed peach tree.

The following is a detailed description of the new variety of peach tree, and the fruit which the same bears:

*Tree.*—The tree is of large size, vigorous, upright, dense, vase-formed, hardy, and a very productive and regular bearer. The trunk of the tree is of medium size, and has a medium bark.

The branches are stocky, medium, and of a dull grey color. The lenticels are numerous and of medium size. The leaves are large, ovate, acuminate, and acutely pointed; such leaves averaging six to eight inches in maximum length and one and one-quarter to one and three-fourths inches in maximum width.

*Leaves.*—The leaves are of medium thickness, smooth, and of medium green color. The margin is glandular and finely serrate, while the petiole is of medium length and thickness. The glands average eight in number, are alternate, and relatively small, reniform, green in color, and are positioned two on the petiole at the leaf base, with the remainder on the leaf. Stipules are lacking.

*Flowers.*—The flower buds are hardy, of medium size and length, plump, free, and pubescent. Under average conditions the dates of first and full bloom of the flowers is on or about March 1st and March 10th, respectively. The flowers bloom at a medium time as compared with other varieties, and are of medium size, and salmon color.

*Fruit.*—The fruit is of uniform, large size and averages two and seven-eighths inches in axial diameter, and three and one-eighth inches transversely in the suture plane. In form the fruit is uniform, broadly oblate, and compressed toward the suture. The suture is a deep line which extends from the base to beyond but discontinuous at apex, and has a slight depression beyond the pistil point. The ventral surface is strongly lipped, and the lips are unequal. The cavity is flaring and is elongated in the suture plane, with the suture showing on one side.

The cavity averages three-fourths of an inch in depth and three-fourths of an inch in breadth. The marking of the cavity is a red blush at suture or opposite side. The base is rounded, and the apex is short and depressed.

The skin is of medium thickness and toughness, free, and has no tendency to crack. The color is predominately deep reddish, slightly mottled, and down or fuzz is almost totally lacking.

The flesh is yellow, mottled with red next to the stone. The surface of the pit cavity is pink, with pink fibres. Amygdalin is wanting; juice is abundant and rich; and the texture is fine and meaty. The fibres are few and fine, and the fruit ripens evenly.

The flavor of the fruit is subacid, and the aroma is scant. The eating quality of the fruit is of the best.

The stone of the fruit is free; the fibres short; and such stone parts from the flesh smoothly. The stone is small, averaging one and one-half inches in length, one inch in breadth, and three-fourths of an inch in thickness. The form of the stone is obovoid; the base straight; the hilum narrow and oval; the apex acuminate; the sides equal and curved on the right side; and the surface furrowed and ridged near the base, and pitted throughout. The ridges are rounded; the pits elongated; the ventral edge thin, with wing toward the base; and the dorsal edge full, with deep narrow groove to above center. The ridges on either side are interrupted, and the color of the stone is brown, with no tendency to split in the wet or dry seasons.

The dates of first and last picking of the fruit, under normal conditions, are approximately August 9th to August 20th, respectively.

The variety has good resistance to insects and diseases.

The fruit of the above described new variety is an excellent market peach for table and dessert use, for the reasons that in addition to its retention of the desirable and tasty flavor of the Elberta and Fay Elberta varieties, it is distinctive in its higher coloring, and almost total lack of down or fuzz, both of which enhance its eye appeal, and further it has good keeping and shipping qualities, as are essential to a successful market peach.

The tree and its fruit, as above described, may vary in certain slight details due to climatic and soil conditions under which the variety may be grown.

Having thus described my invention, I claim:

A new and distinct variety of peach tree substantially as herein disclosed, characterized by freestone fruit having a substantially higher coloring, which is predominately a deep reddish color, and an almost total lack of fuzz; both as compared to the Elberta and Fay Elberta varieties, but retaining the rich flavor of the fruit of said varieties and equaling the latter in ability to bear, tree vigor, size of crop, freedom from disease, and keeping quality of the fruit.

FRED D. WILLIAMS.

REFERENCES CITED

The following references are of record in the file of this patent:

UNITED STATES PATENTS

| Number | Name | Date |
|---|---|---|
| Pl. Pt. 92 | Blake | Apr. 3, 1934 |